(12) United States Patent
Skvirsky et al.

(10) Patent No.: US 9,498,306 B2
(45) Date of Patent: Nov. 22, 2016

(54) DEVICE FOR REMOVABLE ATTACHMENT OF DENTAL PROSTHESIS

(71) Applicants: Igor Skvirsky, Givat-Koah (IL); Leonid Monassevitch, Hadera (IL); Yaniv Skvirsky, Givat-Koah (IL)

(72) Inventors: Igor Skvirsky, Givat-Koah (IL); Leonid Monassevitch, Hadera (IL); Yaniv Skvirsky, Givat-Koah (IL)

(73) Assignee: SKVIRSKY, LTD, Bnei Brak (IL)

( * ) Notice: Subject to any disclaimer, the term of this patent is extended or adjusted under 35 U.S.C. 154(b) by 50 days.

(21) Appl. No.: 14/397,859

(22) PCT Filed: May 30, 2013

(86) PCT No.: PCT/IL2013/050466
§ 371 (c)(1),
(2) Date: Oct. 29, 2014

(87) PCT Pub. No.: WO2013/183042
PCT Pub. Date: Dec. 12, 2013

(65) Prior Publication Data
US 2015/0118647 A1 Apr. 30, 2015

(30) Foreign Application Priority Data

Jun. 4, 2012 (IL) .......................................... 220137

(51) Int. Cl.
*A61C 8/00* (2006.01)
*A61C 13/265* (2006.01)

(52) U.S. Cl.
CPC ........... *A61C 8/0083* (2013.01); *A61C 8/0048* (2013.01); *A61C 8/0057* (2013.01); *A61C 13/2653* (2013.01)

(58) Field of Classification Search
CPC .................... A61C 8/00; A61C 8/0086; A61C 8/0083; A61C 8/0057; A61C 13/2653; A61C 8/0048
(Continued)

(56) References Cited

U.S. PATENT DOCUMENTS 4,586,902 A 5/1986 Obersat
4,741,698 A 5/1988 Andrews
(Continued)

FOREIGN PATENT DOCUMENTS

CH 659383 A5 1/1987
DE 29601514 U1 3/1996
(Continued)

*Primary Examiner* — Nicholas Lucchesi
(74) *Attorney, Agent, or Firm* — Avery N. Goldstein; Blue Filament Law (57) ABSTRACT

The present invention relates to a device for the attachment of dental prosthesis, consisting of a male component which can be anchored into a jaw and a removable attachable female component for receiving the artificial teeth. The device includes at least one spring element and at least one retention element. At least one spring element is a leaf spring element which is made of superelastic material and connected by one of its end to a removable female component or the installed male component of the dental prosthesis and has a convex part on its second end for tight friction contacting with the retention element of opposite component of the dental prosthesis.

19 Claims, 9 Drawing Sheets

(58) Field of Classification Search
USPC .................................................. 433/173, 177
See application file for complete search history.

(56) References Cited

U.S. PATENT DOCUMENTS

| | | | |
|---|---|---|---|
| 4,773,859 A | | 9/1988 | Obersat |
| 5,002,489 A | | 3/1991 | Fischer et al. |
| 5,275,560 A | | 1/1994 | Obersat |
| 5,284,441 A | * | 2/1994 | De Siqueira ......... A61C 13/225 433/177 |
| 5,588,837 A | | 12/1996 | Rubeling et al. |
| 2011/0171599 A1 | | 7/2011 | Seo et al. |
| 2012/0003608 A1 | | 1/2012 | Bluemli et al. |

FOREIGN PATENT DOCUMENTS

| | | |
|---|---|---|
| DE | 102007012880 A1 | 9/2008 |
| DE | 10036825 A1 | 2/2012 |
| EP | 0064601 A2 | 11/1982 |
| RU | 70118 U1 | 1/2008 |

* cited by examiner

DEVICE FOR REMOVABLE ATTACHMENT OF DENTAL PROSTHESIS

BACKGROUND OF THE INVENTION

1. Field of the Invention

The present invention relates generally to a removable dental prosthesis. More particularly, the present invention relates to a novel precision attachment device for securing a removable dental prosthesis in the mouth.

Being more detailed, the present invention relates to a device for the attachment of dental prosthesis, comprising a male component which can be anchored into the jaw and a removably attachable female component for receiving the artificial teeth, whereby the male component includes a retention surface and the female component includes a spring element for retaining the male component near the retention surface.

2. Background of the Invention

During the course of various dental procedures, a dental prosthesis may be installed in the mouth which is secured onto adjacent fixed dentition. Mentioned prosthesis may be carried out as a full denture, overdenture, partial denture, or the like. Such dental prosthesis is arranged so that it can be secured to the fixed dentition, where it is removable under various conditions. For example, partial dentures and removable bridge work are securely inserted in a place in the mouth.

However, for cleaning and maintenance, they must be removable.

Numerous devices have been provided for this purpose, all of which provide both the fixed and removable features. The critical aspect of such devices is to retain the dental prosthesis secured in position during actual use so as to avoid all types of rotation, lateral movement, and displacement of the removable prosthesis from its proper position in the mouth. Any such movement or displacement can cause a disturbance and annoyance to the patient during use.

Numerous holding devices of the above type have been known in the art. For example, Rubeling Gunter in Europatent application EP 0064601 A2 discloses a method for producing dental replacement parts, in which a metal secondary part is detachably anchored via holding elements to a likewise metallic, fixed primary part. Elements serve as a holding bar or "Friktionsstifte" (Friction pin), for the corresponding images with an exact fit in the primary and secondary sections must be created. To date we have drilled these recordings in the primary part or milled. The receptacle for the holding element in the secondary part has been formed during casting. This procedure does not ensure accurate fit and is not applicable to non-precious alloys. According to the present invention will now create the recordings by spark erosion. To ensure perfect fit between the holding member and the absorbency even under tooth replacement parts from a non-precious metal alloy is achieved.

In U.S. Pat. No. 5,588,837 Rubeling Gunter discloses a method and an equipment for forming prosthetic tooth structures for fastening to implants, where at least one pattern is produced from the portion of a patient's jawbone containing the implants and pattern sockets of metal is arranged in it at a place which corresponds with the position of the implant in the patient's jawbone, and a prosthetic tooth structure is produced from metal with the aid of the pattern. The particular feature of the invention consists in the provision of implant electrodes of metal, the heads of which correspond essentially with the heads of the implants, being fastened releasably in the pattern sockets in lieu of dummy implants, and the pattern socket and/or the implant electrodes as well as the prosthetic tooth structure are connected to a spark erosion equipment in such a way that the pattern sockets and/or the implant electrodes form the one electrode and the prosthetic tooth structure the other electrode, and the pattern and the prosthetic tooth structure are moved one against the other, and in so doing the prosthetic tooth structure is eroded so that it is adapted to the heads of the implants.

Andrews Douglas in U.S. Pat. No. 4,741,698 discloses a dental implant which comprises a frame which is attachable to the mandibular or maxillary bone, the frame bearing bar retention means; a detachable bar having complementary bar retention means for removably attaching of the detachable bar to the frame; and denture bearing denture bar retention for attaching the denture to the detachable bar.

Bluemli Marcus et al. in their U.S. patent application 2012003608 disclose the device for fastening a dental prosthesis includes a bar patrix and a connecting part, which can be attached to the dental prosthesis and has a recess into which the bar patrix can be inserted and which is surrounded by two side walls connected via a ceiling element. The side walls and the ceiling element are shaped such that the dental prosthesis, when it is placed on the bar patrix via the connecting part attached thereon, rests on the bar patrix via a first, a second and a third support location, wherein in each case a free space is present between the first and third support locations and the second and third support locations.

Seo Young et al. in U.S. patent application 2011171599 etc. disclose the shape memory dental retention systems which facilitate the adjustment or removal of an oral appliance, e.g., a crown or bridge, from a reconfigurable abutment assembly. The adjustable abutment assembly may be secured to an anchoring implant bored into the bones within the mouth. The abutment assembly has a projecting abutment portion with one or more shape memory material sleeves or plates or elements extending along the abutment. Each of the sleeves has a length with at least one curved or arcuate portion. Energy may be applied to the elements such that the arcuate portion flattens to allow for the oral appliance to be placed thereupon while removal of the energy allows the elements to reconfigure into its curved configuration thereby locking the oral appliance to the abutment. Removal of the oral appliance may be effected by reapplication of energy to the elements.

Obersat Adam in U.S. Pat. No. 5,275,560 discloses a friction element particularly for anchoring one removable telescopable part of a dental prosthesis on another. The one part has an opening through it in which the friction element is disposed. The friction element has a shank in the opening and has a friction head with a friction surface above the part and at one end of the opening. The friction element is of resilient plastic material. The friction head has a tapering, conical or convex bottom side and the opening in the one part is correspondingly shaped. The shank of the friction element has radial tabs which resiliently engage the inside of the opening. The shank may be of a length and the opening may be so shaped that one friction tab is behind the opening and engages the other side of the one part for preventing removal of the friction element. A detent recess in the other part receives the friction head on the telescoping of the parts together.

In his another inventions—U.S. Pat. Nos. 4,586,902 and 4,773,859 Obersat Adam disclose the detachable component of a dental prosthesis which is releasably secured to the permanently installed component by one or more pairs of male and female detent members. Each male detent member has a miniature flat brick-shaped compartment for a flat serpentine (particularly U-shaped or S-shaped) or a flat block-shaped spring whose front portion can bias or constitute a plunger which extends from the compartment and snaps into the respective female detent member. The male detent member or members are mounted on the detachable component and the female detent member or members are provided in or on the permanently installed component, preferably very close to the gum of the respective jaw. The casing which defines the compartment of the male detent member can be a prefabricated part or it may be formed, at least in part, during casting of the metallic part or parts of the detachable component. The overall dimensions of the male detent member need not exceed 5×3.5×1 mm.

In U.S. Pat. No. 5,002,489 Fischer Arthur et al. disclose a dental prosthesis comprises an element fixed in a mouth, a removable dental prosthesis component placed on the element, and a removable connection of the dental prosthesis component with the element and including vertical groove formed in an adjacent surface in each of the element and the component, the grooves being located immediately opposite to one another and open into one another, the connection further including a resilient friction element engaging in the grooves.

In presently known attachments (see, for example, U.S. Pat. No. 4,773,859) of the above out-lined character, the male detent member comprises a flexible or bendable spring which is receivable in the recess of the female detent member (also known simply as female). The flattest conventional male detent member uses a spring which is made of wire having a diameter of 0.7 mm or thereabout, and such wire is inserted into a compartment with certain freedom of movement for penetration into or expulation from the recess of the female detent member. The overall thickness of the male detent member including the receptacle for the spring is in the range of 2 mm.

SUMMARY OF THE INVENTION

The devices described below provide mechanisms and methods to facilitate the adjustment or removal of an oral appliance or prosthesis, such as a full denture, overdenture, partial denture, or the like, from an abutment assembly (by means of natural teeth or implant). In utilizing the abutment assemblies described herein, an anchoring implant can be bored into the bones within the mouth of the patient to provide the structural support of the abutment assembly. Moreover, the implants and abutment assemblies described herein may be utilized in any number of locations within the mouth of a patient, for instance, along the maxilla or mandible or other locations within the body which may benefit from an adjustable abutment assembly as described herein.

One example of an abutment retaining assembly may have a projecting abutment portion. A threaded pin may extend from the lower abutment portion for attachment to the implant, which may be bored into the underlying bone to serve as an anchor. Portions of the abutment retaining assembly may be fabricated from any number of biocompatible materials, e.g., gold alloys, stainless steel nickel-titanium alloys, etc., and may be sized for positioning along a patient's dentition.

According to one embodiment of the present invention, there is provided a device for the removable attachment of dental prosthesis. At least one, dental prosthesis comprises an installed male component which can be anchored into a jaw and a removable attachable female component for receiving an artificial teeth.

According to the preferred embodiment of the present invention, the installed male component includes at least one retention element, such as the female component includes at least one spring element for its retaining according to male component by at least one retention element.

According to the another embodiment of the present invention, the female component includes at least one retention element, such as the installed male component includes at least one spring element for retaining female component according to male component by at least one retention element.

According to both aforementioned embodiments of the invention, at least one spring element is connected by one its end to the removable female component or the installed male component and has the convex part on its second end for friction contacting with the opposite component.

At least one spring element is made as a leaf spring element, which is connected by one its end to a removable female component or the installed male component of the dental prosthesis and has the convex part on its second end for tight friction contacting with at least one retention element of opposite component of the dental prosthesis. At least one spring element may be rigidly connected by one of its end to the removable female component or the installed male component of the dental prosthesis.

According to the most preferred embodiment of the present invention, at least one spring element is made of superelastic material. It may be made of wire or flat plate of superelastic material such as nickel-titanium alloy, coated by polymer, composite or ceramic.

According to the most preferred embodiment of the present invention, this superelastic material is nickel-titanium alloy, which is known as nitinol or NiTi alloy.

According to the most preferred embodiment of the present invention, at least one spring element has the convex part on its second end. The convex part on the second end of at least one spring element has a curve radius less than a curve radius of the first end of the spring element.

According to the other embodiment of the present invention, the second convex part of the spring element has the thickness which is thicker than the thickness of the first convex part of the spring element.

According to the still other embodiment of the present invention, the second convex part of the spring element has the stiffness which is different from the stiffness of the first convex part of the spring element.

According to the further embodiments of the present invention, at least one spring element has the bifurcated or the zigzag convex parts on its second end. The spring element may have also the zigzag convex parts on its both ends.

According to the still other embodiment of the present invention, the first part of the spring element has the width which is wider than the width of the second convex part of this spring element. This first part of this spring element may have also at least one notched side.

According to the further embodiments of the present invention, the first part of the spring element has at least one orifice and/or protrusion for reinforcing the connection with the removable female component of the prosthesis.

According to the further embodiments of the present invention, the first and the second parts of the spring element are symmetric but have the different stiffness.

According to the further embodiments of the present invention, the first and the second parts of the spring element are interchangeable.

According to the further embodiments of the present invention, at least one spring element may have also the convex parts on its both ends.

According to the further embodiments of the present invention, at least one spring element may have the convex parts on its both ends and the additional bulge outside or inside of one of the convex parts.

And then, according to the further embodiments of the present invention, at least one spring element may have the convex parts on its both ends and the additional mounting bulge outside of the middle part of the spring element.

These devices and techniques are well suited for, among other applications, patient removable prostheses, overdentures, bridges and any implant-based dental restoration.

BRIEF DESCRIPTION OF THE DRAWINGS

The objects and advantages of the present invention as well as other objects and advantages will become evident upon consideration of the drawings wherein:

FIG. 5 (a-b) are the enlarged, cutaway views of the latching mechanism in its removable state;

FIG. 8 (a-e) are the exploded cross sectional views of the spring assembly according to the present invention;

FIG. 9 (a-f) illustrates a method of manufacturing the frame of female component for the dental prosthesis, and FIG. 10 (a-f) illustrates one of the embodiments of the spring elements mounting on the frame of the dental prosthesis female component.

DETAILED DESCRIPTION OF THE INVENTION

Figure 1:
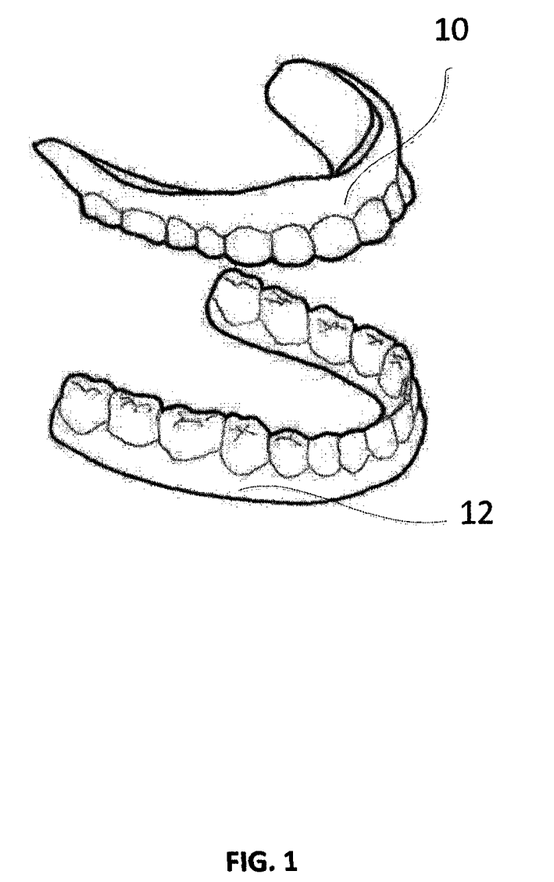
FIG. 1 is a perspective view of the upper and lower dental prostheses.
Figure 2:
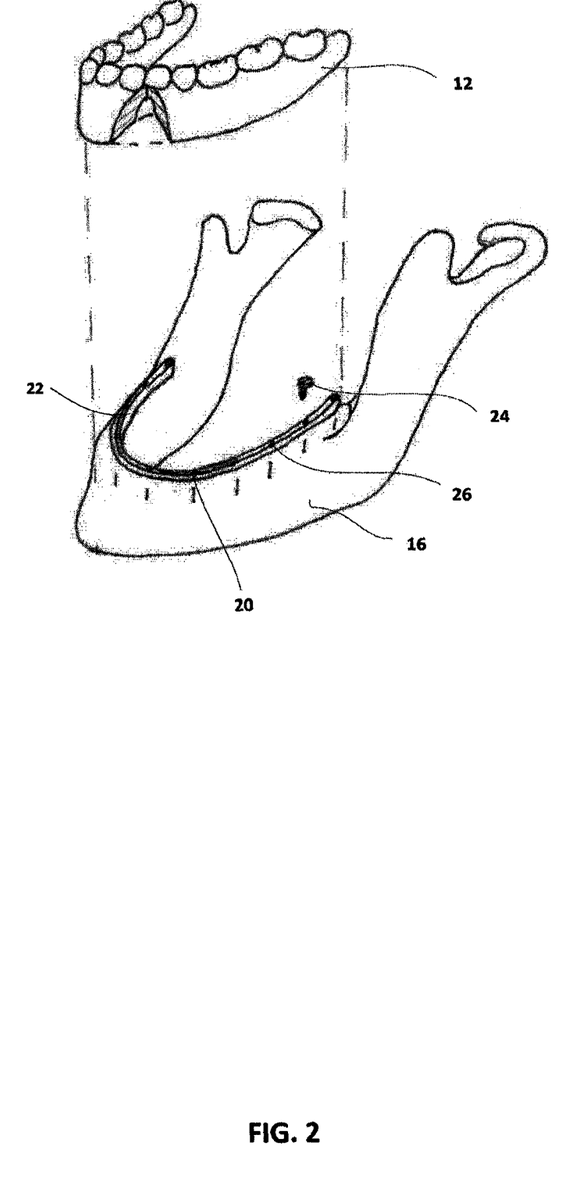
FIG. 2 is a perspective view of a lower jaw with a support bar implant system and removable female component.

Referring to FIG. 1, there is illustrated a perspective view of the removable upper and lower dental prostheses, correspondingly 10 and 12. Referring to FIG. 2, there is illustrated a perspective view of a fixed removable lower implant prosthesis 12. According to the existing technology, the principles of fixation of artificial prostheses are shown in details in the example of lower dental prosthesis 12 (see FIG. 2). Lower dental prosthesis 12 is lean on male component 20 comprising support bar 22 anchored in jaw 16 by means of plurality of screws 24 which extend downwardly from support bar 22 through abutments 26. Abutments. 26 are surgically implanted into jaw 16. Screws 24 (or other securing means) are recessed in support bar 22.

Figure 3:
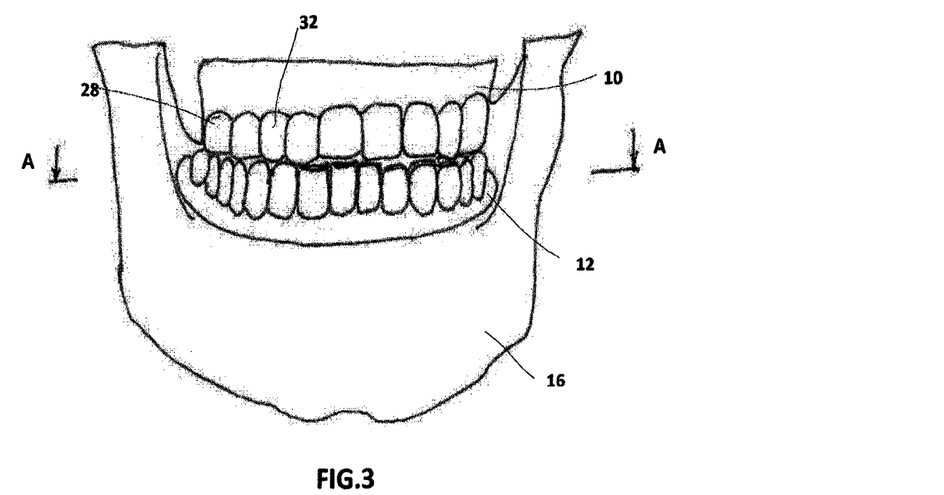
FIG. 3, 4 is an extensive view and a top view of the supra structures further illustrating the lower jaw support bar.

Referring to FIG. 3, there is illustrated an extensive view of the removable upper and lower dental prostheses, correspondingly 10 and 12.

Figure 4:
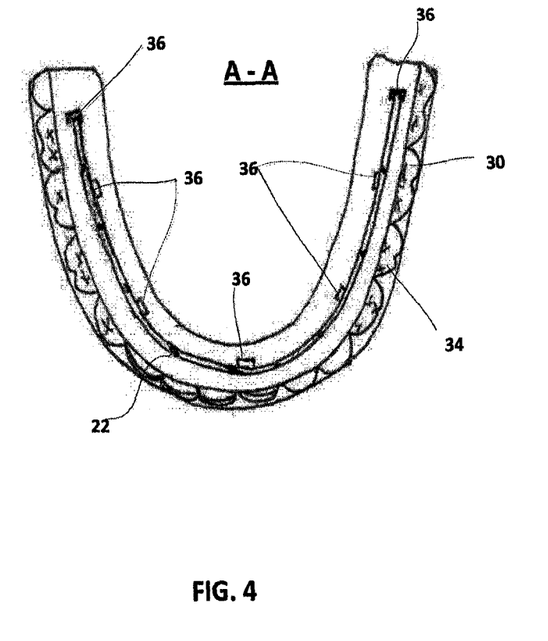

Referring to FIGS. 3, 4, there is illustrated a view of the supra structures and the lower jaw 16 support bar 22. Supra structures 28 and 30 comprise the secondary female components, correspondingly 32 and 34 having some of internally-depending spring elements 36 fit within the retention elements, for example recesses 38 (see FIG. 5 a, b) of support bar 22. In final form, artificial teeth 40 and labial flare 42 are secured to the supra structures 28 and 30. The means for securing these female components such as supra structures 28, 30 to bars 22 have at least one spring element 36 attached to each of supra structures 28, 30.

According to other embodiment of the present invention, supra structures 28, 30 may have some spring elements 36 attached in the middle or attached to opposing ends of these supra structures 28, 30 (see FIG. 4). Mentioned spring elements 36 may be co-operable with the retention elements such as recesses 38 of support bars 22 (FIG. 5) made in underlying support structure of male component 20. These spring elements 36 and recesses 38 were normally placed on the interior, rear, opposing ends of the supra structures 28, 30 (see FIG. 5) and support bar 22. Mentioned spring elements 36 can be cooperable immediately with the side surface of support bars 22 (not shown in the drawings), without recesses 38. By a similar way a removable dental prosthesis can be attached not only to support bar 22, but also to a telescopic or conical tooth crown (not shown in the drawings).

According to still other embodiment of the present invention (not shown in the drawings), spring elements 36 are attached vice versa to the male components 20 whereas recesses 38 are made in female components—supra structures 28, 30.

Figure 5:
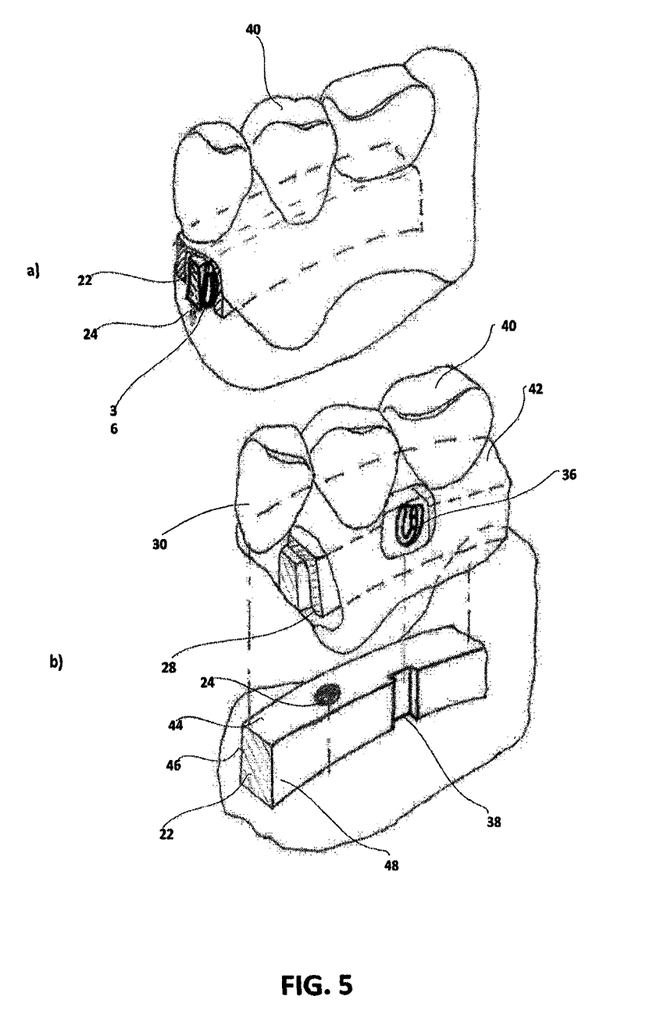

In order to understand better the relationship between the male component—support bar 22 and the supra structure 30 as it shown on. FIG. 5 which is a perspective view of the supra structure 30. Supra structure 30 is arcuate in shape as a result of the conventional fabrication process as described by Gunter Rubeling in U.S. Pat. No. 5,588,837. The supra structure is coincidental with the shape of the support bar 22 having a substantially flat inner top surface 44 and tapered interior sidewalls to coincide with the tapered sidewalls 46 and 48 of support bar 22.

While the supra structure and the support structure is solved by the spark erosion fabrication process and the cooperation between supra structure 30 and support bar 22, the dental technician, on behalf of the end user, must be still ensured that the supra structure will be secured to the support bar 22 such as that there will be no vertical displacement between the supra structure and the support bar 22, particularly during the eating process. Inventors have developed the new and improved attachment means—spring elements 36 which provides tight and reliable contact between support bars 22 and supra structures 28, 30 in order to maintain them in a vertically secure manner and inventors have also developed a procedure which ensured the close tolerances required in order to maintain a secure fit over a long period of time.

The installed male component—support bars 22 may include at least one retention element-lateral surface or recess 38 (see FIG. 5), such as the female component includes at least one spring element 36 for its retaining according to male component—support bar 22 by at least one retention element, for example, recesses 38. The inventors propose various forms of execution of spring element 36 (see FIG. 6 (a-f) and FIG. 7 (a-f).

Figure 6:
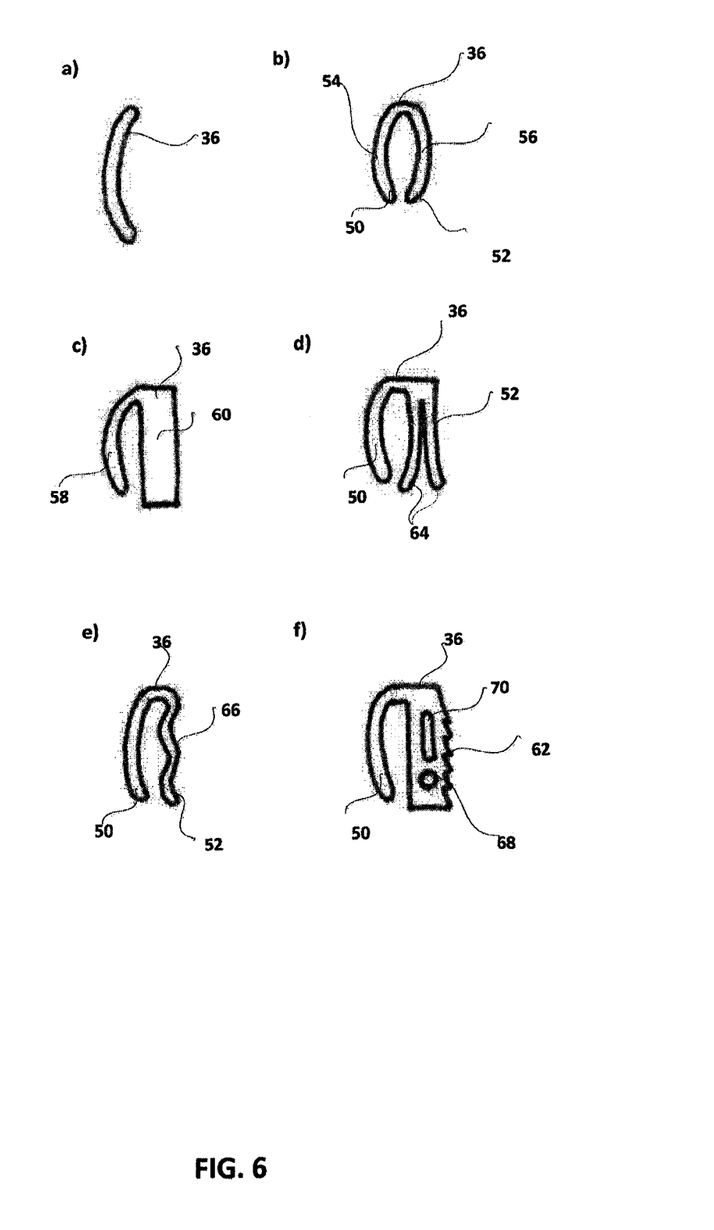
FIG. 6, 7 (a-f) are the exploded perspective views showing the different types of the locking spring elements according to the present invention.

According to the most preferred embodiment of the present invention, at least one spring element 36 is made of super-elastic material (FIG. 6-a). It may be made of wire or flat plate of superelastic material such as nickel-titanium alloy, which is known as nitinol or NiTi alloy. This alloy may be coated by polymer, composite or ceramic.

Spring element 36 (FIG. 6-b) has end 50 and end 52 with the convex parts 54 and 56. Convex part 54 on end 52 of at least one spring element 36 has a curve radius less than curve radius of convex part 56 on end 50 of spring element 36.

According to the embodiment of the present invention, shown in FIG. 6-*b*, convex part 56 of spring element 36 has the thickness which is thicker than the thickness of convex part 54 of spring element 36.

According to other embodiment of the present invention, (not shown in the drawings), convex part 56 of spring element 36 has the stiffness which is different from the stiffness of convex part 54 of spring element 36.

According to the embodiment of the present invention, shown in FIG. 6-*c*, part 60 of spring element 36 has the width which is wider than the width of convex part 58 of this spring element 36. This second part 60 of this spring element may have also at least one notched side 62 (see FIG. 6-*f*).

According to the embodiment of the present invention (shown in FIG. 6-*d, e*), spring element 36 has bifurcated 64 or zigzag 66 convex parts on its second end 52.

According to the embodiments of the present invention, shown in FIG. 6-*f*, one of the parts of spring element 36 has at least one orifice 68 and/or protrusion 70 for reinforcing the connection with the removable female component—supra structures 28, 30 of the prosthesis.

According to the further embodiment of the present invention (see FIG. 6-*b*), the first and the second parts, correspondingly 50 and 52 of spring element 36, are symmetric but have the different stiffness.

And then according to the last embodiments of the present invention, the first part 50 and the second part 52 of spring element 36 can be made interchangeable (see FIG. 6-*b*).

According to some other embodiments of the present invention, at least one spring element 36 is made of superelastic material (FIG. 7*a-f*). It may be made of wire or flat plate of superelastic material such as nickel-titanium alloy, which is known as nitinol or NiTi alloy. This alloy may be coated by polymer, composite or ceramic.

Figure 7:
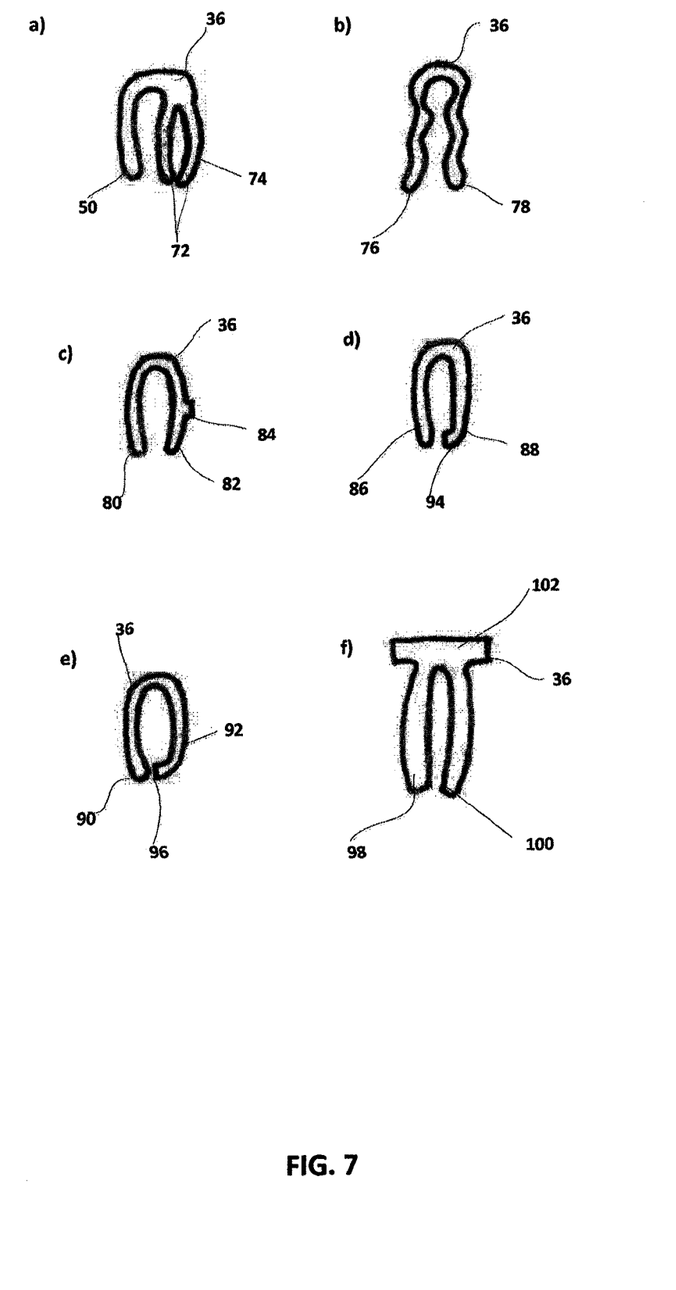

According to the embodiment of the present invention, shown in FIG. 7-*a*, spring element 36 has first end 50 and bifurcated convex part 72 on its second end 74. Spring element 36, shown in FIG. 7-*b* has two zigzag convex parts 76 and 78.

According to the embodiment of the present invention, shown in FIG. 7-*c*, spring element 36 has two convex parts on its both ends 80 and 82 with the additional bulge 84 outside of one of convex parts, for example, convex part 82.

According to the other embodiments of the present invention, shown in FIG. 7-*d, e*, spring elements 36 have two convex parts, on their both ends correspondingly 86, 88 and 90, 92 with the additional bulge, correspondingly 94,96 inside of one of convex part, for example, convex part 88 and 92.

And then, according to still other embodiment of the present invention, shown in FIG. 7-*f*, spring element 36 has the convex parts on its both ends 98 and 100; and additional mounting bulge 102 outside of the middle part of this spring element.

These spring elements 36 and techniques are well suited for, among other applications, patient removable prostheses, overdentures, bridges and any implant-based dental restoration. The removable prosthesis with spring elements of the proposed design can be fixed not only on support bar, but also on natural teeth or implants.

Figure 8:
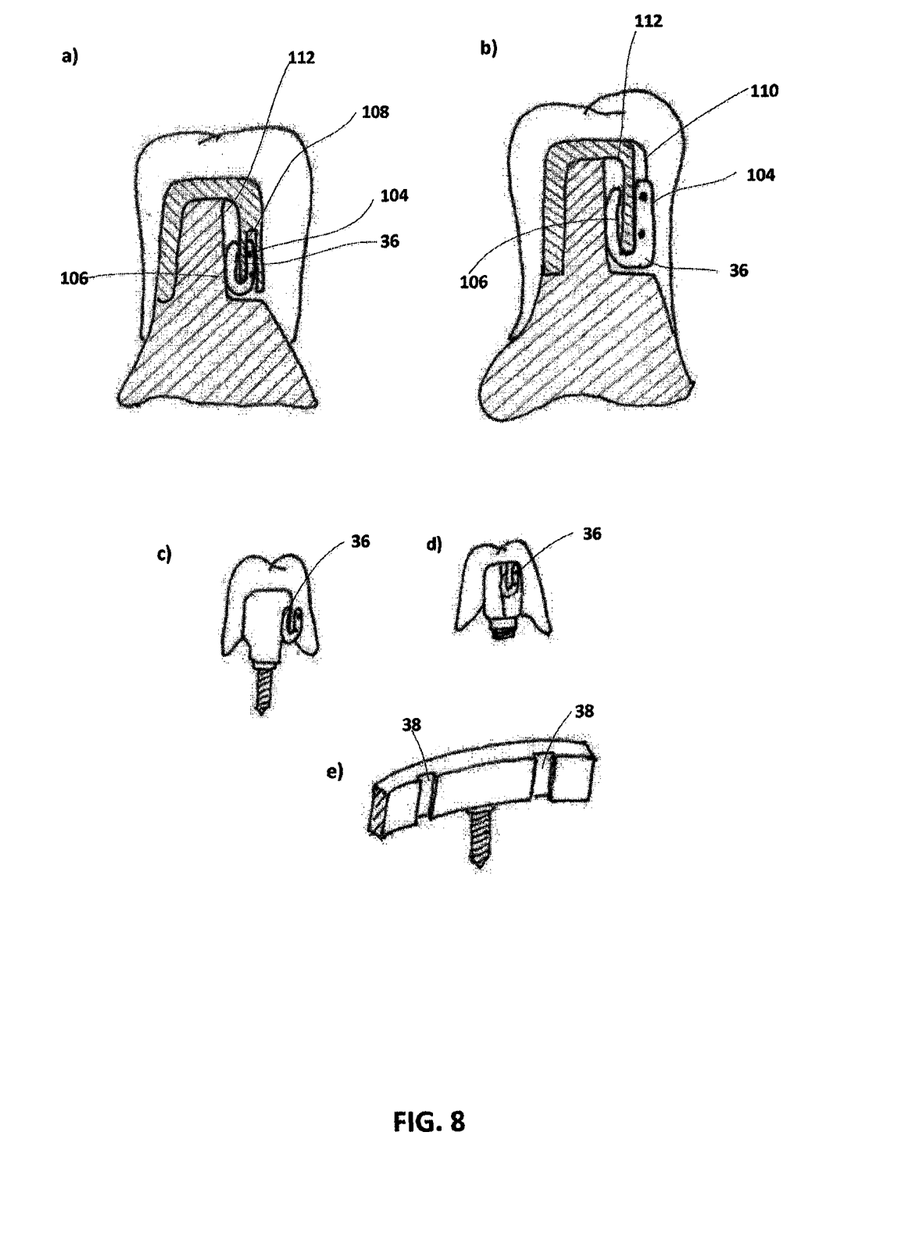

Referring to FIG. 8-*a, b*, at least one spring element, which is made as leaf spring element 36, is connected by one its end 104 to the removable female component—supra structure 28 or 30 and has convex part 106 on its second end for friction contacting with the retention element, for example, recess 38 (FIG. 8-*e*) of opposite component.

The inventors also proposed a variant of fastening different types of spring elements 36 (see FIG. 6 *a-f* and FIG. 7 *a-f*) on the installed male component 20 of the dental prosthesis, when these spring elements 36 have the convex parts on its second end for tight friction contacting with at least one retention element of opposite female component of the dental prosthesis (see FIG. 8-*c, d*).

According to this variant, spring element 36 may be rigidly connected by one of its ends to the installed male component 20 of the dental prosthesis.

The present invention is used as follows:

Referring to FIG. 4, the area surrounding spring elements 36 in labial flare 42 has been cut away to illustrate the manner in which the supra structure 30 is secured to support bar 22 by way of securing spring elements 36. At least one spring elements 36 is rigidly secured into female component 30 by one of conventional method (for example by rivets or screws), and then secured within recess 38 which extends on exterior side wall 48 to support bar 22. Thus, it will be recognized that the axis of the channel of female component 30 as it approaches coincidental with the axis of the support bar 22 will provide the tight contact both of female 30 and male 22 components. Achieving this, preferable arrangement is dictated by the size of the prosthesis and its positioning within the mouth. Spring element or spring elements 36 thus secures the supra structure 30 and attached artificial teeth 40 in a secure manner to the support bar 22. The manner of achieving this secure fit by means of a tight frictional engagement between spring elements 36 and the wall of recess 38 as they extend into the support bar 22 is achieved by the fabrication method which will be described hereafter.

For this secure fit achievement, spring elements 36 can be produced by one of known conventional method such as mechanical bending or stamping with a possible subsequent heat treatment or laser cutting of a plate, spark erosion fabrication process, photochemical (photo-etching) methods or other methods of metals forming.

The purpose of the fixed removable implants is to allow an individual having a dental prosthesis 10, 12 the opportunity to remove the prosthesis for care and cleaning of the prosthesis as well as the underlying support structure—bar 22 and gums without the necessity of a dental visit. It is therefore desirable that the securing means which secures the artificial teeth and supra structures 28, 30 to the underlying support bar 22 would be easily accessible to the prosthetic wearer as well as being secured in some manner such that it is not lost, swallowed or misplaced when the prosthesis is removed.

Inventors have addressed that problem in the instant matter by having spring elements 36 rigidly secured on the female component—supra structure 30 and having these spring elements 36 attached within a longitudinal slit of supra structure 30 which would be co-operable with recesses 38. In this manner, the prosthetic wearer can grasp the exterior parts of supra structure 30 which is graspable with a fingernail on the exterior of the labial flare 42 and pull supra structure 30 outwardly disengaging it from the support bar 22, while at the same time limiting its outward motion by means of spring elements 36 so that spring elements 36 are disengaged from support bar 22. In this manner, the female component—supra structure 30 and accompanying artificial teeth 40 can be removed for hygienic purposes.

An example embodiment of using a removable dental prosthesis with the proposed attachment according to the present invention will be described below:

The attachments or couplings for dental prostheses include male component 20 comprising support bar 22 anchored in jaw 16 by means of plurality of screws 24, and supra structures 28 and 30 comprising the secondary female components, correspondingly 32 and 34. A male 20 and a female 32, 34 components intended to cooperate in a press button like a manner to fix a dental prosthesis in the mouth.

Usually the anchoring means such as support bar 22 and supra structures 28 and 30 comprising the secondary female components, correspondingly 32 and 34 of these couplings are made of titanium and because this material is well tolerated in the mouth and of a great mechanical resistance to ensure the good working of the assembly despite the very small dimensions of these elements. With time, the metal on metal friction of these parts causes a non-negligible wear which hinders good securement of the prosthesis which then wobbles.

The aim of the present invention is to provide a coupling for a dental prosthesis tending to remedy this drawback and this is obtained thanks to the female part of such a coupling which is distinguished by the fact that it comprises some of internally-depending spring elements 36 fit within the retention elements such as recesses 38 (see FIG. 5 a, b) of support bar 22. The surface of this spring elements 36 and recesses 38 are polished or smooth.

The female components, correspondingly 32 or 34 of the coupling shown comprises a housing of metal, generally titanium, or any other suitable material, which has on its outside surface anchoring formation, for example grooves 108 or 110 (see FIG. 8-a, b) enabling the fixing of said housing by means of spring elements 36, rigidly attached to these grooves.

Therefore, in coupled position, convex parts 106 on the second ends of spring elements 36 enter in contact with recesses 38 fixing surface of support bar 22 of the coupling and cause the locking of the assembly. In the example shown in FIG. 8-a, b is provided so that the coupling obtained is said to be "static", i.e. without play.

Spring elements 36 of the proposed design can be located with respect to support bar 22 transversely or longitudinally, in particular, longitudinally on the ends of support bar 22 (see FIG. 4) or longitudinally in the special longitudinal through grooves, made in this bar 22.

Spring elements 36 made of superelastic material such as nickel-titanium alloy, which is known as nitinol or NiTi alloy and may be coated by polymer, composite or ceramic.

A very important technological point for spring element 36 is that the height of the chord of convex part 106 of spring element 36 would be larger than the width of the gap 112 between the side wall of female component 32, 34 and side wall of bar 22. According to a similar design of spring elements 36, it does not require a particularly high precision in the manufacture of recesses 38.

In other non-illustrated variants of spring elements 36 for the fixing of dental prostheses, their manufacturing could be realized in other ways than described here above. For example, it is possible to manufacture the spring elements 36 with two interchangeable (for example, symmetric parts), when one of these parts is fixed softer, and the other—harder. This can be achieved, for example, due to different thermal treatment of these parts.

Provisions are also different ways of rigid fixing spring elements 36, for example, by making them a part of an extended, bifurcated, zigzag-shaped, etc. Spring elements 36 may be rigidly fixed in one of their parts by rivets, screws, pins, etc.

There are also can be made the kits of spring elements 36 of varying shape and stiffness. The technicians, who produce the dental prosthesis, can take from these kits the necessary spring elements 36 for the manufacturing of specific prosthesis for specific patients.

By selecting the spring elements 36 from the set, proposed the inventors, the manufacturers of artificial dental prosthesis and technicians can achieve a secure mounting of removable dentures in the mouth. At the same time, patients receive high quality, reliable dental prostheses.

Figure 9:
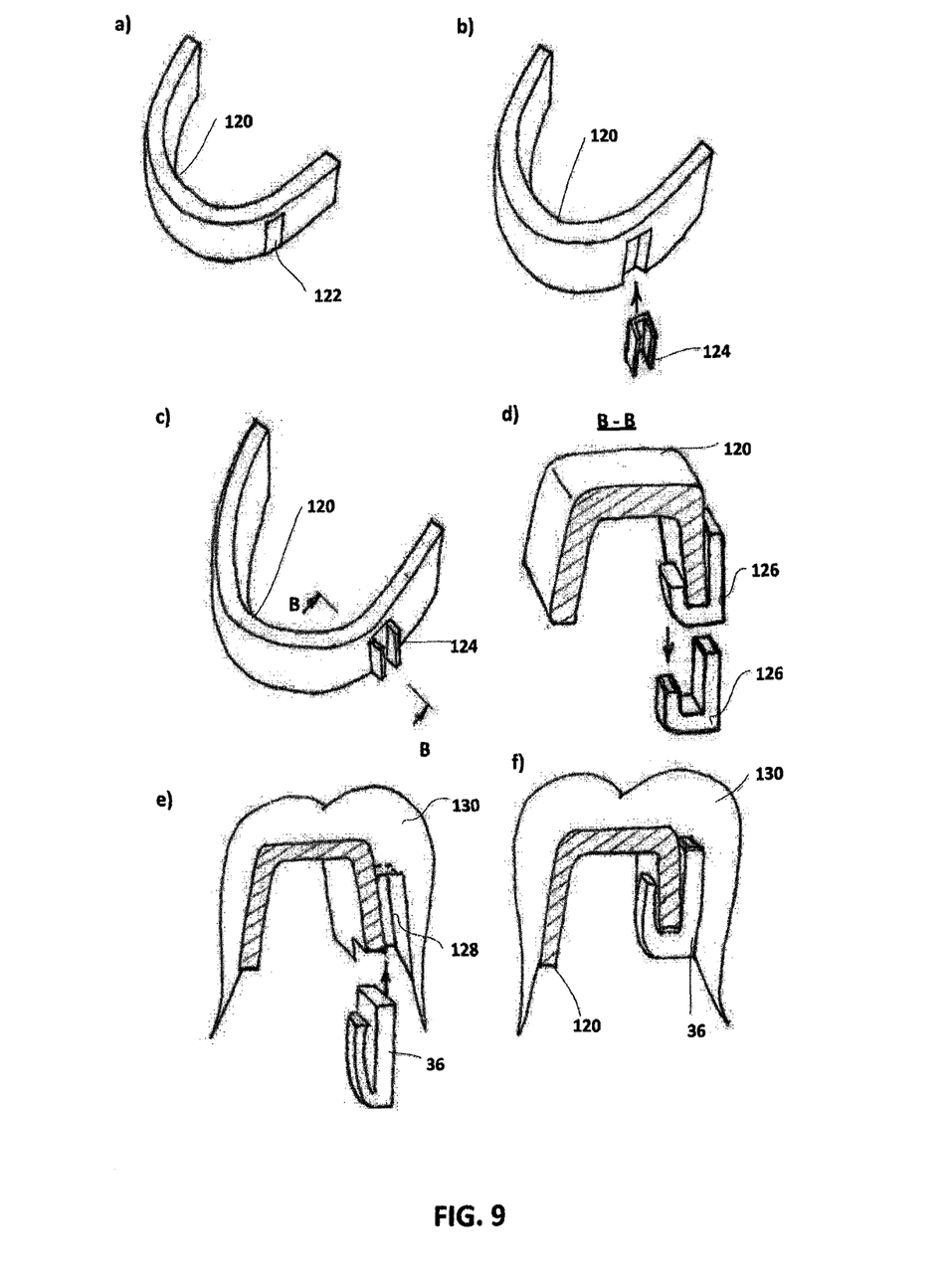

The method for producing the dental prosthesis with the inventive device for removable attachment is accomplished in a fashion similar to, but different than, conventional prosthesis producing methodologies. Regardless of the technique employed, a negative bone impression is presented to the dental laboratory. The dental laboratory can make a positive model poured from dental stone (a convention dental gypsum product) so that the frame design can be created thereon. Next, the dental laboratory manufactures frame 120 of supra structure 28 or 30 (see FIG. 9-a). Frame 120 is made of cobalt-chromium or nickel-chromium or other biocompatible dental metal or alloy by precision investment casting. During this process, in frame 120, in the places of the future installation of spring elements 36 are performed before depression 122 filled with removable material such as a wax or a special plastic. Then the removable material is extracted from the mentioned depression 122 and there shall be established pre-casting inserts 124 (see FIG. 9-b, c), and then spacers 126, which serve to form grooves 128 for the future installation of spring elements 36. The cross-sectional view B-B of the frame 120 together with the attached spacer 126 is shown in FIG. 9-d. Spacer 126 is made of metal and will be removed after the final manufacture of the dental prosthesis (see FIG. 9-d). After installing all spacers 126, frame 120 with spacers 126 is placed in a mold and filled with material (plastic), imitating natural teeth 130. After cooling the casting denture, it removes all of spacers 126 and remains grooves 128 for the installation of spring elements 36 (FIG. 9-e, f).

After the final casting, the resulting structure is cleaned, polished, in grooves 128 there are installed spring elements 36 and supra-structure 28 or 30 is ready for use.

Figure 10:
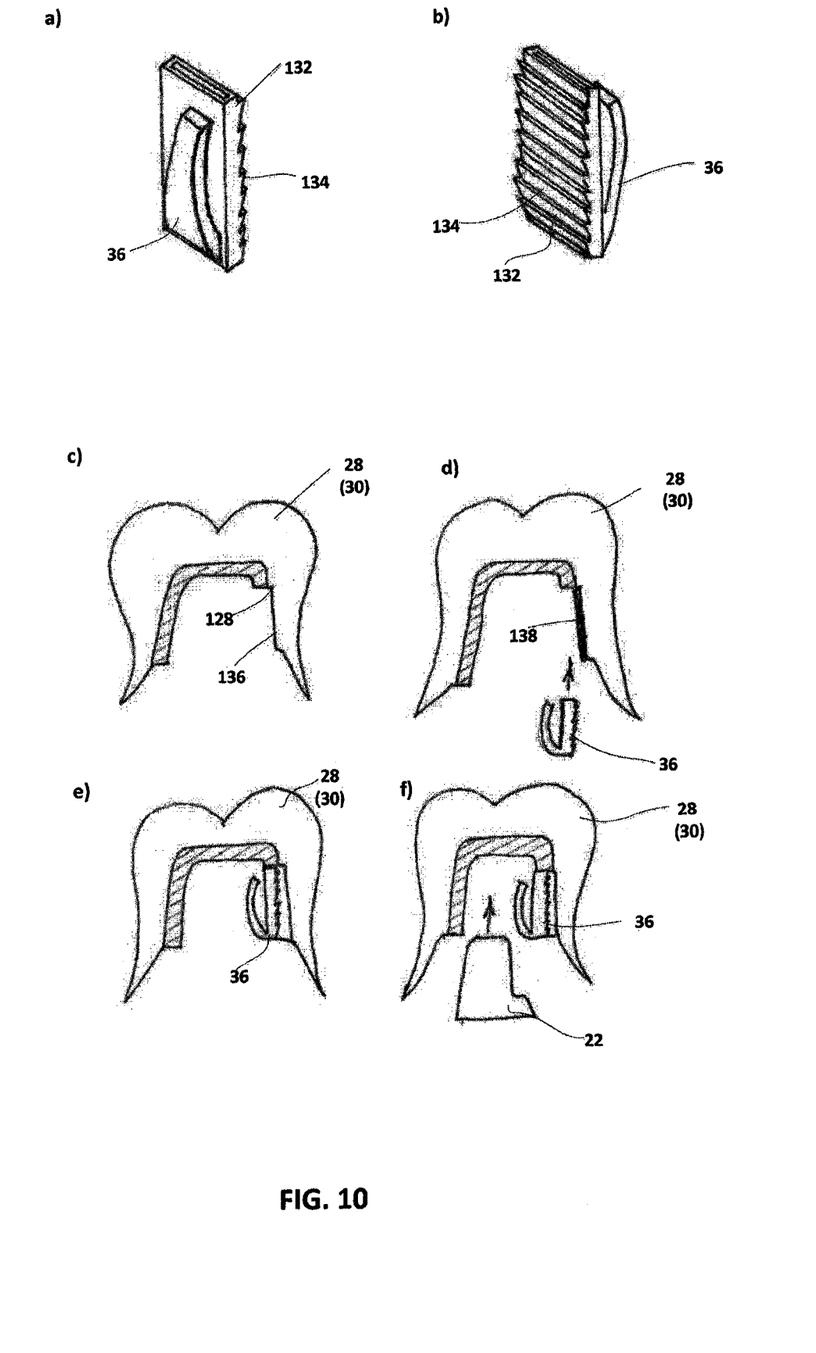

The installation of spring elements 36 may be implemented as shown in FIG. 10 a-f. On the mounting surface 132 of spring element 36 can be made notches 134 (see FIG. 10-a, b). Similar notches 136 may be performed on the inner surface of the groove 128 of supra-structure 28 or 30. In addition, the inner surface of groove 128 may be covered by layer 138 of adhesive material such as glue or dental cement or a special plastic. Spring elements 36 are rigidly mounted in grooves. 128 with an adhesive material. Supra-structure 28 or 30 is finally ready to be used by installation on support bar 22 or on a telescopic or conical tooth crown (not shown in the drawings).

While the present invention has been described in connection with the exemplary embodiment thereof, it will be understood that many modifications will be apparent to those of ordinary skill in the art and that this application is intended to cover any adaptations or variations thereof. Therefore, it is manifestly intended that this invention only be limited by the claims and the equivalents thereof.

The invention claimed is:

1. A device for the removable attachment of dental prosthesis, comprising:

an installed male component which can be anchored into a jaw;

a removable attachable female component for receiving artificial teeth, said installed male component or removable attachable female component includes at least one recessed retention element;

one of said female component and said male component includes at least one spring element for retaining the other of said female component and male component, said at least one spring element is made of superelastic material and has a U-shaped configuration formed by a first convex part for connection to one of said removable female component and said installed male component and a second convex part for friction contacting with said recessed retention element of the other of said removable female component and said installed male component.

2. The device according to claim 1, wherein the second convex part of said at least one spring element is a leaf spring.

3. The device according to claim 2, wherein the first convex part of said at least one spring element is rigidly connected to one of the removable female component and said installed male component.

4. The device according to claim 1, wherein said at least one spring element is made of wire of superelastic material.

5. The device according to claim 1, wherein said at least one spring element is made of flat plate of superelastic material.

6. The device according to claim 1 wherein said superelastic material is nickel-titanium alloy, which is known as nitinol or NiTi alloy.

7. The device according to claim 1, wherein said superelastic material is nickel-titanium alloy, coated by polymer, composite or ceramic.

8. The device according to claim 1, wherein said second convex part of said at least one spring element has a maximal curve radius less than the maximal curve radius of the first convex part of said spring element.

9. The device according to claim 1, wherein said second convex part of said at least one spring element has a thickness which is thicker than a thickness of the first convex part of said spring element.

10. The device according to claim 1, wherein said second convex part of said spring element has a stiffness which is different from a stiffness of the first convex part of said spring element.

11. The device according to claim 1, wherein said second convex part of at least one spring element has a bifurcated shape.

12. The device according to claim 1, wherein said second convex part of said at least one spring element has a zigzag shape.

13. The device according to claim 1, wherein said first and second convex parts of said at least one spring element have a zigzag shape.

14. The device according to claim 1, wherein said first convex part of said at least one spring element has a width which is wider than a width of the second convex part of said spring element.

15. The device according to claim 1, wherein said first convex part of said at least one spring element has at least one notched side.

16. The device according to claim 1, wherein said first convex part of said at least one spring element has at least one orifice and/or protrusion for reinforcing the connection with the removable female part of the prosthesis.

17. The device according to claim 1, wherein said first and second convex parts of said at least one spring element are symmetric but have a different stiffness.

18. The device according to claim 17, wherein said first and second convex parts of said at least one spring element are interchangeable.

19. The device according to claim 1, wherein said at least one spring element has an additional bulge on one of said convex parts.

* * * * *